United States Patent
Choi et al.

(10) Patent No.: US 8,318,969 B2
(45) Date of Patent: Nov. 27, 2012

(54) ALIGNMENT MATERIAL FOR LIQUID CRYSTAL DISPLAY DEVICE OF VERTICAL ALIGNMENT MODE AND METHOD OF PREPARING THE SAME

(75) Inventors: Jin wook Choi, Hwaseong (KR); Eung jae Park, Hwaseong (KR); Jae cheol Park, Hwaseong (KR); Yong bae Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 1030 days.

(21) Appl. No.: 12/281,328

(22) PCT Filed: Feb. 9, 2007

(86) PCT No.: PCT/KR2007/000713
§ 371 (c)(1),
(2), (4) Date: Sep. 1, 2008

(87) PCT Pub. No.: WO2007/097537
PCT Pub. Date: Aug. 30, 2007

(65) Prior Publication Data
US 2009/0041955 A1 Feb. 12, 2009

(30) Foreign Application Priority Data
Feb. 22, 2006 (KR) .......... 10-2006-0017150

(51) Int. Cl.
*C07C 229/00* (2006.01)
(52) U.S. Cl. ......... 560/46; 428/1.26; 528/289; 528/310; 560/43; 560/64

(58) Field of Classification Search .......... 428/1.26; 528/289, 310; 560/43, 46, 64
See application file for complete search history.

(56) References Cited

U.S. PATENT DOCUMENTS
2008/0069968 A1* 3/2008 Cherkaoui et al. .......... 427/487

OTHER PUBLICATIONS
USPTO structure search, Jan. 2012.*

* cited by examiner

*Primary Examiner* — Gregory Listvoyb
(74) *Attorney, Agent, or Firm* — Lexyoume IP Meister, PLLC.

(57) ABSTRACT

This invention provides alignment materials for liquid crystal display device of vertical alignment mode and methods for the preparation of the same, and more particularly, it provides diaminobenzene derivatives represented by the following formula 1:

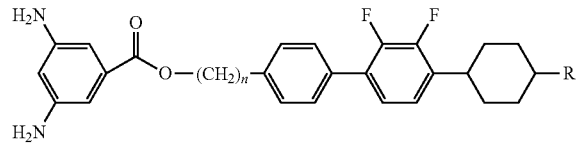

wherein n is an integer of 1 to 5 and R is an alkyl or alkoxy group of 3 to 5 carbon atoms, which align liquid crystal in uniform and vertical way, have not only excellent mechanical properties such as heat resistance and surface strength but also high pretilt angles of liquid crystal and in particular, can make response rate of liquid crystal fast, methods for the preparation of the same and liquid crystal alignment films using the same.

8 Claims, No Drawings

ALIGNMENT MATERIAL FOR LIQUID CRYSTAL DISPLAY DEVICE OF VERTICAL ALIGNMENT MODE AND METHOD OF PREPARING THE SAME

TECHNICAL FIELD

This invention relates to alignment materials for liquid crystal display device of vertical alignment (hereafter, VA) mode and more particularly, to diaminobenzene derivatives which align liquid crystal in uniform and vertical way, have not only excellent mechanical properties such as heat resistance and surface strength but also high pretilt angles of liquid crystal and in particular, can make response rate of liquid crystal fast, methods for the preparation of the same and liquid crystal alignment films using the same.

BACKGROUND ART

Alignment films are formed on portions connected directly to liquid crystal molecules in liquid crystal display devices, and as a functional thin film controlling the alignment of liquid crystal molecules, materials for alignment films have a very important role in determining the display characteristics of liquid crystal display devices.

Currently, a variety of polymer compounds have been known as compounds used for liquid crystal alignment materials. Of them, the mostly-used representative compounds are polyimide based polymer compositions which use polyamic acids through imidization. Also, according to the documents that have been known so far, a variety of polymer compositions such as polyacryis, polyvinyls, and polyamides substituting the hydrogen atom of amide bond with other monovalent organic group have been proposed. However, as they involve insufficient problems in alignment properties of liquid crystal molecules, electrical-optical characteristics, coating performance, heat resistance, drug resistance, etc., very few cases have been put to practical use.

Polyimide has been used as insulating materials, protection materials, etc. in electric and electronic material fields due to its inherent high mechanical intensity, heat resistance and solvent resistance and it has also been spotlighted as materials for liquid crystal alignment films of current liquid crystal display devices because films can be easily formed uniformly and it has excellent durability. Recently, however, as technologies about liquid crystal display devices are developing, new characteristics that did not exist for materials for liquid crystal alignment films before are required.

Basic requisites for liquid crystal alignment films are the control of pretilt angles. It has been known that the pretilt angles of liquid crystal molecules are greatly affected by the shape of the surface of alignment films and the length of side chains. In particular, liquid crystal display devices of VA mode require high pretilt angles of 88-90 degree. Generally, as means for obtaining high pretilt angles, there have been used side-chained polyimide compounds. However, it is difficult to obtain alignment having uniformly high pretilt angles throughout the whole regions of broad substrates by the mere use of side-chained polyimide compounds. To obtain such high pretilt angles, there have been developed polyimide liquid crystal alignment materials using as a monomer, an aliphatic side-chained diamine having a straight alkoxy group or un-saturated alkyl group as a side chain, but as the distribution and length of the side chains are not controlled in such polyimide alignment films, their pretilt angles were often as low as 3~25 degree or so.

For example, Japanese Patent Laid-Open No. 5-043687 describes liquid crystal display devices using liquid crystal alignment films using polyimide resins having as a repeat unit, a compound represented by the following structure 1:

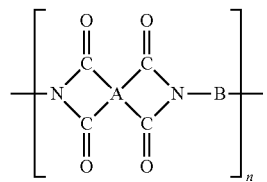

wherein A is a tetravalent organic group constituting tetracarboxylic acid and its derivatives, B is a bivalent organic group constituting diamine, and n is an integer.

However, it was difficult to obtain pretilt angles around 90 degree by using the above polyimide alignment film, and after-image frequently occurred. Furthermore, the mixtures of polyimides and polyamic acids were separated by heat, and liquid crystal alignment materials prepared by the block copolymerization of the polyimides and polyamic acids involved too complicated preparation routes.

Also, Korean Patent Laid-Open No. 2004-0069565 discloses diaminobenzene derivatives having a long-chained alkyl group or alkylcyclohexylphenyl group as a side chain and polyimide liquid crystal alignment films using the same.

DISCLOSURE OF INVENTION

Technical Problem

In order to solve the problems of the prior arts, it is an object of the invention to provide a diaminobenzene derivative that is an alignment material for liquid crystal display devices of vertical alignment node, which aligns liquid crystal in uniform and vertical way, has not only excellent mechanical properties such as heat resistance and surface strength but also high pretilt angles of liquid crystal and in particular, can make response rate of liquid crystal fast, a method for the preparation of the same and a liquid crystal alignment film using the same.

Technical Solution

To achieve the aforementioned objects, the present invention provides a diaminobenzene derivative represented by formula 1:

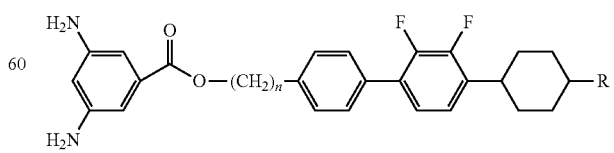

wherein n is an integer of 1 to 5 and R is an alkyl group or alkoxy group of 3 to 5 carbon atoms.

Further, the invention provides a method for the preparation of the side-chained diamine compound represented by formula 1 as defined above comprising:

a) preparing a compound of formula 3:

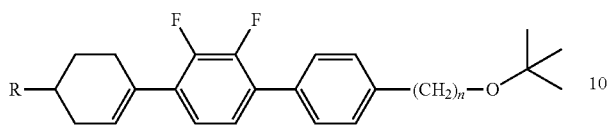

wherein n is an integer of 1 to 5 and R is an alkyl group or alkoxy group of 3 to 5 carbon atoms by reacting a compound of formula 2:

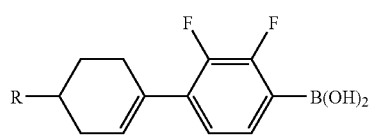

wherein R is an alkyl group or alkoxy group of 3 to 5 carbon atoms, with 1-bromo-4-(3-tert-butoxy-alkyl)-benzene, tetrakis(triphenylphosphine)palladium, cesium fluoride and 1,2-dimethoxy-ethane;

b) preparing a compound of formula 4:

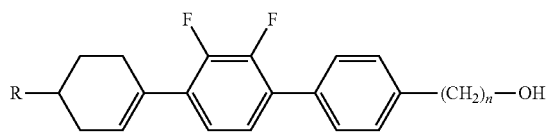

wherein n is an integer of 1 to 5 and R is an alkyl group or alkoxy group of 3 to 5 carbon atoms by reacting the compound of formula 3 with acetic acid and bromic acid and then reacting it with potassium carbonate and methanol;

c) preparing a compound of formula 5:

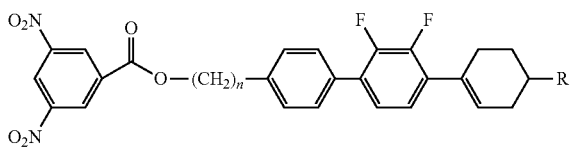

wherein n is an integer of 1 to 5 and R is an alkyl group or alkoxy group of 3 to 5 carbon atoms by reacting the compound of formula 4 with triethylamine, tetrahydrofuran, and 3,5-dinitrobenzoylchloride; and d) hydrogen reducing the compound of formula 5 under a Pd/C catalyst and separating a trans isomer compound therefrom.

Still further, the invention provides a method for the preparation of a polyimide resin for vertical alignment material of liquid crystal display device comprising:

a) preparing a polyamic acid based block copolymer by reacting the compound of formula 1 as defined above, a tetracarboxylic acid dianhydride of formula 6:

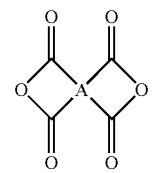

wherein A is a tetravalent organic group, and a diamine compound having no side chain group of formula 7:

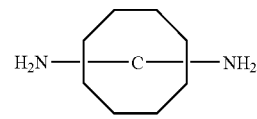

wherein C is a bivalent organic group having no side chains, under a solvent; and b) converting the polyamic acid based block copolymer into a polyimide through ring-closing dehydration by thermal treatment.

Still further, the invention provides a polyimide resin for vertical alignment material of liquid crystal display device having a weight average molecular weight of 1,000 to 200,000 prepared by the above method.

Still further, the invention provides a liquid crystal alignment film prepared by using the above polyimide resin for vertical alignment material of liquid crystal display device.

Still further, the invention provides a liquid crystal display device comprising the above liquid crystal alignment film.

Advantageous Effects

The side-chained diamine compounds of formula 1 of the present invention are useful for the manufacturing of polyimide resins for non-rubbing vertical alignment materials, and the polyimide resins prepared using the diamine compounds have good vertical alignment of liquid crystal and can exert pretilt angles of 89 or more with non-rubbing methods regardless of rubbing process conditions and furthermore, the polyimide resins in accordance with the invention have reduced response rate and thus they are useful as alignment material for liquid crystal display device.

MODE FOR THE INVENTION

This invention is further described in detail.

The liquid crystal alignment materials according to the invention comprise an alkyl chain group, aromatic ring and 2,3-difluorophenyl group as functional side chains as shown in above formula 1 by being designed to have the side chains so that they align liquid crystal in uniform and vertical way, have not only excellent mechanical properties such as heat resistance and surface strength but also high pretilt angles of liquid crystal and in particular, can make response rate of liquid crystal fast.

The alkyl chain located on the terminal of the side chain can exert vertical alignment properties, lower surface tension and create spaces into which organic solvents can penetrate between polymer chains, thereby increasing solubility. The polyimides themselves that have the mere alkyl chain as a side chain fail to exhibit vertical alignment properties. Also, the aromatic ring holds liquid crystal molecules vertically and further, their rigid core group and terminal alkyl group are linked in such a bar shape as liquid crystal and thus can increase vertical alignment properties by the interaction with the lateral sides of the liquid crystal when the liquid crystal was placed around the side chains. In addition, 2,3-difluorophenyl group induces a strong dipole moment in the direction of the short axis of diamine molecule. This dipole moment in the short axis direction of the molecule, unlikely the direction of the long axis of the diamine compound, renders the side chain of the polyimide to move along with the liquid crystal compounds when electric field is applied and the restoring force of the side chain as well as the restoring force of liquid crystal to co-operate when the electric field is removed, thereby remarkably shortening the response rate.

Also, the side chain containing polyimide resins determine the length of diamine side chains and the length between the side chains, depending on the average length of the long axis of the liquid crystal molecules and the size of required pretilt angles. Preferably, the length of the side chain group in the side-chained diamine compounds of formula 1 above is determined such that the ratio of the length of the polyimide side chain group and the average length of the long axis of the liquid crystal molecules is within the range of 0.8 to 1.5. The width between the side chain groups is an important factor in determining the density of side chain groups arranging on substrate surface. Therefore, it is preferable to insert diamine compounds having no side chains into the main chain of the polyimides such that the length between the polyimide side chain groups becomes 1.5 to 3.5 times the length of the liquid crystal molecules.

The side-chained diamine compounds of formula 1 above can be prepared via such methods as reaction flow 1:

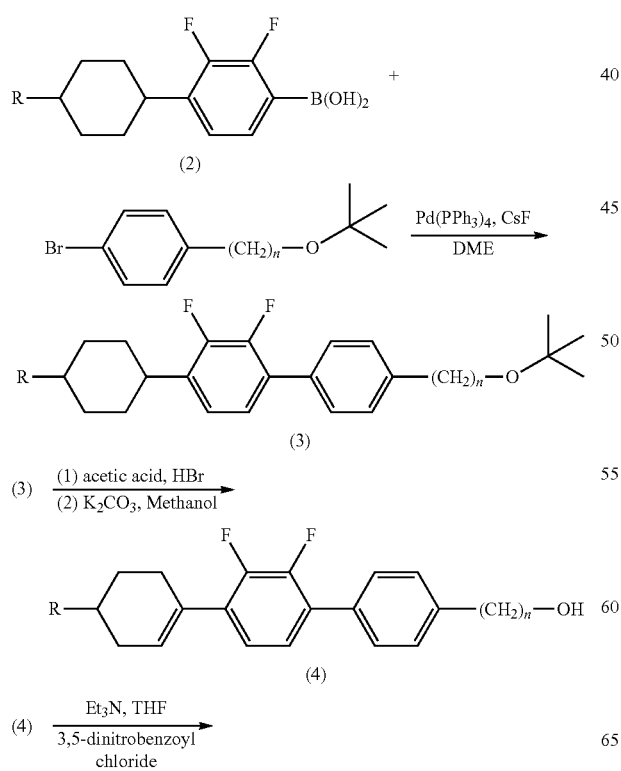

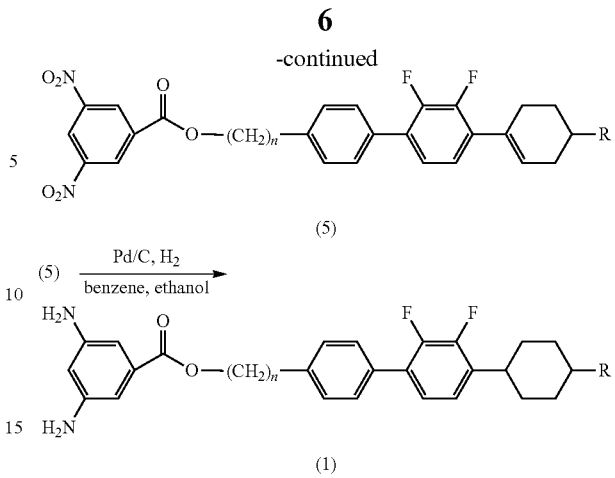

wherein n is an integer of 1 to 5 and R is an alkyl group or alkoxy group of 3 to 5 carbon atoms.

Step 1

4'-(3-Tert-butoxy-alkyl)-2,3-difluoro-4-(4-alkyl-1-cyclohexenyl)-biphenyl of formula 3 above can be obtained by dissolving 1-bromo-4-(3-tert-butoxy-alkyl)-benzene and the compound of formula 2 above in 1,2-dimethoxy ethane, adding a catalytic amount of tetrakis(triphenylphosphine)palladium and 2M cesium fluoride aqueous solution thereto and refluxing them.

Step 2

2,3-Difluoro-4-(4-alkyl-cyclohexenyl-biphenyl-4'-alkyl alcohol of formula 4 above can be obtained by first dissolving the compound of formula 3 above in acetic acid, adding a catalytic amount of bromic acid thereto and reacting them and then, dissolving the obtained compound in methanol, adding 2M potassium carbonate aqueous solution thereto and refluxing them.

Step 3

2,3-Difluoro-4-(4-alkyl-1-cyclohexenyl)-biphenyl-4'-alkyl 3,5-dinitro benzoate of formula 5 above can be obtained by dissolving the compound of formula 4 above in refined tetrahydrofuran, adding a catalytic amount of triethylamine and 3,5-dinitrobenzoylchloride in equivalent ratio thereto and refluxing them.

Step 4

The final diamine compound of formula 1, 2,3-difluoro-4-(4-alkyl-cyclohex)-biphenyl-4'-alkyl 3,5-diamino benzoate can be obtained by hydrogen reducing the compound of formula 5 above under a Pd/C catalyst and separating isomers.

Further, the present invention provides a method for the preparation of polyimide resins using the diamine compound of formula 1 above and the polyimide resins, and the method for the preparation of the polyimide resins is characterized by comprising a) preparing a polyamic acid based block copolymer by reacting a side-chained diamine compound of formula 1 as defined above, a tetracarboxylic acid dianhydride of formula 6:

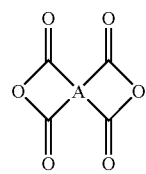

wherein A is a tetravalent organic group, and a diamine compound having no side chain group of formula 7:

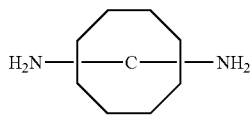

wherein C is a bivalent organic group having no side chains, under a solvent; and b) converting the polyamic acid based block copolymer into a polyimide through ring-closing dehydration by thermal treatment.

As a specific example, tetracarboxylic acid dianhydride of formula 6 above is slowly dropwise added to a reaction solution of the side-chained diamine compound of formula 1 above and the diamine of formula 7 above dissolved in N-methyl-2-pyrrolidone under nitrogen atmosphere for 2 hours while the temperature is being kept at 5-C, and stirred for 6 hours to prepare polyamic acid based block co-polymers. The viscosity can be adjusted by using such cellosolve type solvents as diethyleneglycolmonomethylether, diethyleneglycolmonoethylether, ethyleneglycolmonobutylether, etc.

Then, the polyamic acid based block copolymers can be converted into polyimides having a repeat unit of formula 5 through ring-closing dehydration reaction by thermal treatment between 100 to 230° C. for 30 min to 2 hours.

As the solvents, it is preferable to use inert solvents. Specific examples of the inert solvents are N-methyl-2-pyrrolidone (NMP), N,N-dimethylformamide (DMF), dimethysulfoxide (DMSO), hexamethlphosphoramide, tetramethgenesulfone, p-chlorophenol, p-bromophenol, 2-chloro-4-hydroxytoluene, dioxane, tetrahydrofuran (THF), cyclohexanone and the like.

As tetracarboxylic acid dianhydride of formula 6 above, compounds having a tetravalent organic group can be employed. Their specific examples are 3,3',4,4'-benzophenonetetracarboxlic acid dianhydride, 4,4'-oxydiphthalic anhydride (ODPA), 3,3',4,4'-biphenyletracarboxylic acid dianhydride (BPDA), 1,2,4,5-benzenetetracarboxgic acid dianhydride (PMDA), cis-1,2,3,4-cyclopentanetetracarboxylic acid dianhydride (CPDA), cyclobutanetetra-carboxylic acid dianhydride (CBDA) and 4-(2,5-dioxotetrahydrofuran-3-yl)-1,2,3,4-tetrahydronaphthalene-1,2-carboxylic acid dianhydride (TDA).

Also, as the diamine compounds of formula 7 above, diamine compounds having no lateral substituents can be used. Specifically, there are 4,4'-diaminodiphenylether (ODA), 4,4'-methylenebiscyclohexylamine (PACM), 4,4'-methylene-2-methylcyclohexylamine (ANCAMINE), 4,4'-methylenedianiline, diaminobenzophenone, 4,4'-methylenediphenyldiamine (MDA), 4,4'-hexafluoroisopropyldiphenyldiamine (6FDA), p-phenylenediamine, etc.

The compound included in formula 1 which is the side-chained bivalent organic group in the polyimides is used to confer improvement in response rate properties and vertical alignment properties and the bivalent organic group (C) having no side chains is used to control the width between the side chains and determine the distribution of the side chain groups.

The side chain length of the side-chained bivalent organic group is controlled to be 0.8 to 1.5 times the average length of the long axis of the liquid crystal molecules. Also, it is advisable to determine the type and amount of the bivalent organic group (C) such that the length between the side chains can be 1.5 to 3.5 times the length of the long axis of the liquid crystal molecules. More preferably, the compound of formula 6 in the above is used in the same mole amount as the total moles of the compound of formula 1 and the compound of formula 7 above, and the amount of the compound of formula 1 and the compound of formula 7 is preferably 1:1 to 10 in molar ratio, more preferably 2 to 4. The above method enables the preparation of the polyimide resins having a specific structure, of which the side chains can show excellent vertical alignment properties and improved properties in solubility and membrane permeability. Preferably, the average weight molecular weight of the polyimide resins is 1,000 to 200,000.

Further, the present invention provides liquid crystal alignment films using the polyimide resins, and the liquid crystal alignment films can be obtained by coating the alignment solutions comprising the polyimide compounds onto patterned substrates and then calcining them. The solvents used in the alignment solution are usually used in the liquid crystal alignment solutions and they are not limited to specific ones as long as they can dissolve the polyimide compounds, and the alignment solutions preferably include the polyimide compounds in an amount of 1 to 30% by weight.

Also, the alignment solution can be used by being further blended with diaminosiloxane represented by formula 8:

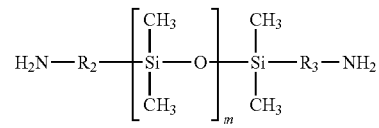

wherein $R_2$ is a bivalent organic group aliphatic or aromatic hydrocarbon group having 3 to 6 carbon atoms, and m is an integer of 1 to 100, in order to increase adhesion to substrate surface. Preferably, the diaminosiloxane is included in an amount of 0.1 to 20% by weight.

The liquid crystal alignment films of the present invention align liquid crystal in uniform and vertical way, have not only excellent mechanical properties such as heat resistance and surface strength but also high pretilt angles of liquid crystal and in particular, can make response rate of liquid crystal fast.

The present invention will be described in detail by reference to the following examples, by which the invention is not limited in any way.

EXAMPLES

Example 1

The diamine compounds of formula 1 were synthesized by reaction flow 1. Synthesis in each step is as follows.

(Step 1)

2.5 g (9.26 mmol) of 1-bromo-4-(3-tert-butoxy-propyl)-benzene and 3.11 g (0.0111 mol) of 1,2-difluoro-3-(4-propyl-1-cyclohexenyl)-benzene boronic acid were dissolved in 90 ml of 1,2-dimethoxyethane. 90 ml of 2M cesium fluoride aqueous solution and 0.32 g (3 mmol %) of tetrakis(triphenylphosphine)palladium were dropwise added to the reaction solution and then refluxed for 3 hours. The reaction solution was extracted with ether and sodium chloride, then dried over anhydrous magnesium sulfate and distilled under a reduced pressure and then re-crystallized with ethyl acetate and ethanol, affording a white solid (yield: 74%).

Mass: 426(M+), 370, 339, 325, 255, 229, 134, 81, 57

(Step 2)

9.4 g (0.0221 mmol) of 4'-(3-tert -butoxy-propyl)-2,3-difluoro-4-(4-propyl-1-cyclohexenyl)-biphenyl was dissolved in 120 ml of acetic acid and 30 ml of bromic acid and then stirred at 50° C. for 1 hour. Upon completion of the reaction, it was extracted with ether and sodium chloride and the obtained yellow liquid was distilled under a reduced pressure and then dissolved in 100 ml of methanol, followed by the addition of 100 ml of 3.5 M potassium carbonate and then refluxed for 3 hours. Upon completion of the reaction, it was extracted with ether and sodium chloride, then dried over anhydrous magnesium sulfate and distilled under a reduced pressure and then re-crystallized with ethyl acetate and ethanol, affording 2,3-difluoro-4-(4-propyl-1-cyclohexenyl)-biphenyl-4'-propyl alcohol (yield: 92%).

Mass: 370(M+), 352, 313, 274, 255, 201, 91, 55

$^1$H NMR (400 MHz, CDCl$_3$): 7.47 (2H, d), 7.28 (2H, d), 7.10 (1H, m), 7.03 (1H, m), 6.01 (1H, s), 3.71 (2H, t), 2.76 (2H, t), 2.41 (1H, m), 1.90 (4H, m), 1.62 (2H, m), 1.35 (7H, m), 0.93 (3H, t)

(Step 3)

7.0 g (0.0189 mol) of 2,3-difluoro-4-(4-propyl-1-cyclohexenyl)-biphenyl-4'-propyl alcohol was dissolved in 100 ml of refined tetrahydrofuran, followed by the addition of 4.35 g (0.0189 mmol) of triethylamine. 4.35 g (0.0189 mol) of 3,5-dinitrobenzoylchloride dissolved in 100 ml of refined tetrahydrofuran was dropwise added to the reaction solution and refluxed for 3 hours. After the progress of the reaction was checked, the reaction solution was extracted with ether and sodium chloride, dried over anhydrous magnesium sulfate, distilled under a reduced pressure and re-crystallized with ethyl acetate and ethanol, affording 2,3-difluoro-4-(4-propyl-1-cyclohexenyl)-biphenyl-4'-propyl 3,5-dinitro benzoate (yield: 75%).

$^1$H NMR (400 MHz, CDCl$_3$): 9.19 (1H, t), 9.08 (2H, d), 7.46 (2H, d), 7.30 (2H, d), 7.03 (2H, m), 6.02 (1H, s), 4.53 (2H, t), 2.86 (2H, t), 2.36 (2H, m), 2.24 (2H, m), 1.87 (2H, m), 1.65 (1H, m), 1.55 (2H, m), 1.39 (2H, m), 1.32 (2H, m), 0.94 (3H, t)

(Step 4)

5 g (8.86 mmol) of 2,3-difluoro-4-(4-propyl-1-cyclohexenyl)-biphenyl-4'-propyl 3,5-dinitro benzoate was dissolved in 100 ml of ethanol, followed by the addition of 0.5 g of 10% (wt) Pd/C, and then it was stirred at room temperature for 12 hours under a hydrogen pressure of 4.5 kg/cm$^2$. After the completion of the reaction, Pd/C was filtered using cellulite, and the reaction solution was dried over anhydrous magnesium sulfate, distilled under a reduced pressure, and re-crystallized with ethanol, affording 2,3-difluoro-4-(4-alkyl-cyclohexyl)-biphenyl-4'-alkyl 3,5-diamino benzoate (yield: 66%).

$^1$H NMR (400 MHz, CDCl$_3$): 746 (2H, d), 7.28 (2H, d), 7.11 (1H, m), 7.02 (1H, m), 6.77 (2H, d), 6.19 (1H, m), 4.31 (2H, t), 3.68 (4H, s), 2.86 (1H, m), 2.81 (2H, t), 2.10 (2H, m), 1.89 (4H, m), 1.50 (1H, m), 1.35 (4H, m), 1.24 (2H, m), 1.09 (2H, m), 0.91 (3H, m)

Example 2

10.0 g (0.02 mmol) of 2,3-difluoro-4-(4-alkyl-cyclohexyl)-biphenyl-4'-alkyl 3,5-diamino benzoate and 8.0 g (0.04 mol) of 4,4'-diaminodiphenylether (ODA) were dissolved in 170.0 g of N-methyl-2-pyrollidone and the thus obtained reaction solution was added to 19.32 g (0.06 mol) of 3,3',4,4'-benzophenonetetracarboxylic acid dianhydride (BTDA) and reacted for 4 hours while the temperature was being kept at 5° C. The reaction solution was precipitated in excessive amount of deionized water, providing polyamic acid. The polyamic acid solid was washed several times with deionized water using a mixer. Thereafter, it was dried in a vacuum oven of 50° C. for two days, affording polyamic acid solids, and the properties of the obtained polymers are shown in Table 1 below.

Example 3

With the exception that 3,3',4,4'-benzophenonetetracarboxylic acid dianhydride (BTDA) used in Example 2 was replaced by 4,4'-oxydiphthalic acid (ODPA), the same procedures as Example 2 were carried out, affording polyamic acid solids, and the properties of the obtained polymers are shown in Table 1 below.

Example 4

With the exception that 3,3',4,4'-benzophenonetetracarboxylic acid dianhydride (BTDA) used in Example 2 was replaced by 3,3',4,4'-biphenyltetracarboxylic acid dianhydride (BPDA), the same procedures as Example 2 were carried out, affording polyamic acid solids, and the properties of the obtained polymers are shown in Table 1 below.

Comparative Example 1

With the exception that 2,3-difluoro-4-(4-alkyl-cyclohexyl)-biphenyl-4'-alkyl 3,5-diamino benzoate used in Example 2 was replaced by 4'-(4-pentylcyclohexyl)biphenyl-3,5-diamine, the same procedures as Example 2 were carried out, affording polyamic acid solids, and the properties of the obtained polymers are shown in Table 1 below.

The properties were evaluated using the following methods.

1) Weight Average Molecular Weight of Polymers

To calculate the weight average molecular weights of the polymers, gel permeation chromatography (GPC) was measured. Retention time of columns where polymer substances were filled using dimethylacetamide (DMAc) as a mobile phase at 60° C. was measured, and the average molecular weight of the polyamic acid solids was calculated by the adjustment of the retention time and the average molecular weight of stylene polymers. Polymers constituting liquid crystal alignment materials have the weight average molecular weight of 2,000 to 1,500,000 g/mol or so.

2) Imidization Rate

It was calculated by the following mathematical formula 1:

$$T(\%) = \frac{(A_{1380}/A_{1500})r}{(A_{1380}/A_{1500})_{260}} \times 100$$

using change in imide ring C—N stretching absorption strength ($A_{1380}$) at 1380 cm$^{-1}$ with regard to benzene ring C=C stretching absorption strength ($A_{1500}$) at 1500 cm$^{-1}$ according to temperature change in FT-IR measurements.

3) Surface Tension

It was obtained from the relationship between surface free energy (surface tension) of liquid crystal alignment films and contact angles from the contact angle of iodized methylene and the contact angle of pure water which were measured over liquid crystal alignment films in accordance with the methods described in the document (D. K. Owens. J. Appl., Pol., Sci. vol 13. 1741-1747 (1969)). The contact angles were measured using KRUSS DSA100 and obtained by adding water and iodized methylene over the films and calculating the average value of the contact angles for 10 sec.

4) Alignment Properties of Liquid Crystal

When voltage was applied to liquid crystal display devices in on/off mode, the presence/absence of abnormal domains among the liquid crystal cells was observed with a microscope, and when there was no abnormal domain, it was designated 'good'.

5) Pretilt Angle of Liquid Crystal Display Device

It was measured by a crystal rotation method using a He—Ne laser light (632.8 nm) in accordance with the methods described in the document (T J. Schffer, et. al., J., Appl., Phys., vol. 19, 2013 (1980)).

6) Voltage-Holding Ratio of Liquid Crystal Display Device

After the voltage of 5 V is applied to liquid crystal display devices for 60 microseconds, voltage-holding ratio was measured after 1667 milliseconds from the removal of application.

7) Response Rate of Liquid Crystal Display Device

Square waves of +4.4 V~−4.4 V, 60 Hz were applied via a wave generator and after a polarizer and analyzer were adjusted so that where bias voltage was set at 1V, light-receiving level became 0% when applied voltage was removed and light-receiving level became 100% when all the applied voltage was applied, the sun of the time until when light-receiving level reached 90% after the driving voltage was applied and the time until when light-receiving level reached 10% after the driving voltage was removed was measured.

TABLE 1

Table 1 Properties of Obtained Polyamic Acid Derivatives

|  | Number Average Molecular Weight (Mn) | Weight Average Molecular Weight (Mw) | Volume Average Molecular Weight (Mz) | Polydisperse Index (Mw/Mn) |
| --- | --- | --- | --- | --- |
| Ex. 2 | 21000 | 37000 | 58000 | 1.78 |
| Ex. 3 | 29000 | 41000 | 53000 | 1.41 |
| Ex. 4 | 54000 | 61000 | 69000 | 1.13 |
| Com. Ex. 1 | 32000 | 53000 | 78000 | 1.66 |

As seen in Table 1 above, the polyamic acid derivatives of Examples 2 to 4 according to the present invention showed improved permeability when compared with that of Comparative Example 1, and they had the weight average molecular weights of 37,000 to 61,000 and the polydisperse index of 1.13 to 1.78.

Also, the polyamic acid solids prepared in Examples 2 to 4 and Comparative Example 1 were dissolved in a solution of NMP and 2-butoxyethanol which were mixed in a ratio of 4:1 by volume, in an amount of 4% by weight. The thus obtained solution was filtered through a filter of 0.1 um and coated onto a glass substrate with clear conductive films being patterned thereon by a spinner method in a thickness of 600 Angstrong. After coating, it was pre-calcined at 90° C. for 3 min and calcined at 220° C. for 1 hour, and the characteristics of the thus obtained thin film were evaluated and summarized in Table 2 below.

TABLE 2

Table 2 Properties of Polyimide Derivatives Prepared by Heat Curing

|  | Imidization Rate (%) | Surface Tension (dyn/cm) |
| --- | --- | --- |
| Ex. 2 | 100 | 39.52 |
| Ex. 3 | 100 | 40.36 |
| Ex. 4 | 100 | 39.94 |
| Com. Ex. 1 | 99 | 37.56 |

As seen in Table 2, the polyimide films of Examples 2 to 4 showed 100% imidization rate and the surface tension of 39.52 to 40.36 and Comparative Example 1 showed 99% imidization rate and the surface tension of 37.56.

Further, two substrates on which liquid crystal alignment films were formed as above were counter-arranged with a certain space (cell gap) without rubbing the alignment film sides, the surroundings of the two substrate were joined using a sealant, the cell gap defined by the substrate surface and sealant was filled with liquid crystal by injection, and the injection hole was sealed whereby liquid crystal cells were manufactured. The characteristics of the thus produced liquid crystal cells are shown in Table 3 below.

TABLE 3

Table 3 Characteristics of Liquid Crystal Cells

|  | Alignment Properties | Pretilt Angle (Degree) | Voltage-Holding Ratio (%) | Response Rate (ms) |
| --- | --- | --- | --- | --- |
| Ex. 2 | Good | 89.7 | 97.47 | 15.6 |
| Ex. 3 | Good | 89.2 | 96.06 | 16.5 |
| Ex. 4 | Good | 89.0 | 98.79 | 17.0 |
| Com. Ex. 1 | Good | 89.4 | 98.89 | 20.1 |

As seen in Table 3 above, Examples 2 to 4 according to the present invention and Comparative Example 1 all showed excellent vertical alignment by non-rubbing methods and their VHR and alignment properties were excellent. In particular, Examples 2 to 4 showed much faster response rate than Comparative Example 1.

Industrial Applicability

As described in the above, the side-chained diamine compounds of formula 1 of the present invention are useful for the manufacturing of polyimide resins for non-rubbing vertical alignment materials, and the polyimide resins prepared using the diamine compounds have good vertical alignment of liquid crystal and can exert pretilt angles of 89 or more with non-rubbing methods regardless of rubbing process conditions and furthermore, the polyimide resins in accordance with the invention have reduced response rate and thus they are useful as alignment material for liquid crystal display device.

The invention claimed is:

1. A diaminobenzene derivative represented by the following formula:

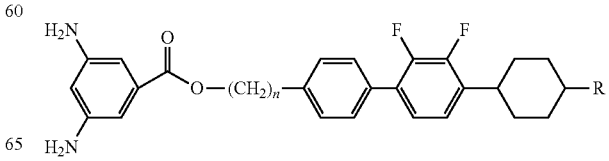

wherein n is an integer of 1 to 5 and R is an alkyl group or alkoxy group of 3 to 5 carbon atoms.

2. A method for the preparation of the side-chained diamine compound represented by formula 1 comprising:
a) preparing a compound of formula 3:

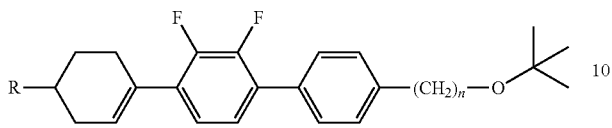

wherein n is an integer of 1 to 5 and R is an alkyl group or alkoxy group of 3 to 5 carbon atoms by reacting a compound of formula 2:

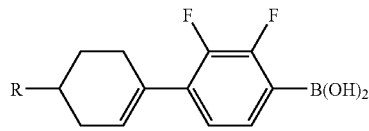

wherein R is an alkyl group or alkoxy group of 3 to 5 carbon atoms, with 1-bromo-4-(3-tert-butoxy-alkyl)-benzene, tetrakis(triphenylphosphine)palladium, cesium fluoride and 1,2-dimethoxy-ethane, b) preparing a compound of formula 4:

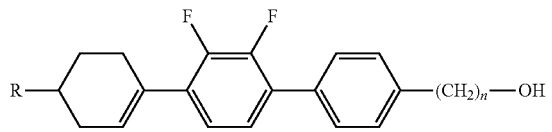

wherein n is an integer of 1 to 5 and R is an alkyl group or alkoxy group of 3 to 5 carbon atoms by reacting the compound of formula 3 with acetic acid and bromic acid and then reacting it with potassium carbonate and methanol;

c) preparing a compound of formula 5:

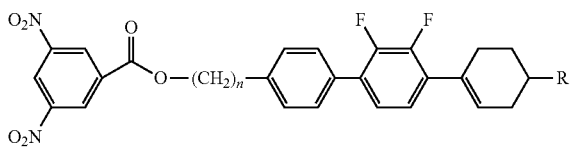

wherein n is an integer of 1 to 5 and R is an alkyl group or alkoxy group of 3 to 5 carbon atoms by reacting the compound of formula 4 with triethylamine, tetrahydrofuran, and 3,5-dinitrobenzoylchloride; and d) hydrogen reducing the compound of formula 5 under a Pd/C catalyst and separating a trans isomer compound therefrom.

3. A method for the preparation of a polyimide resin for vertical alignment material of liquid crystal display device comprising:
a) preparing a polyamic acid based block copolymer by reacting the compound of formula 1 as defined above, a tetracarboxylic acid dianhydride of formula 6:

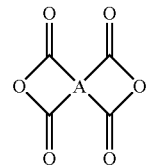

wherein A is a tetravalent organic group, and a diamine compound having no side chain group of formula 7:

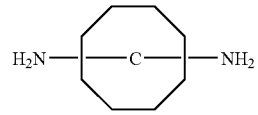

wherein C is a bivalent organic group having no side chains, under a solvent; and
b) converting the polyamic acid based block copolymer into a polyimide through ring-closing dehydration by thermal treatment.

4. The method for the preparation of the polyimide resin for vertical alignment material of liquid crystal display device according to claim 3, wherein the solvent is one or more inert solvents selected from the group consisting of N-methyl-2-pyrrolidone (NMP), N,N-dimethylformamide (DMF), dimethyl-sulfoxide (DMSO), hexamethylphosphoramide, tetramethylenesulfone, p-chlorophenol, p-bromophenol, 2-chloro-4-hydroxytoluene, dioxane, tetrahydrofuran (THF) and cyclohexanone.

5. A polyimide resin for vertical alignment material of liquid crystal display device having a weight average molecular weight of 1,000 to 200,000 prepared by the method as described in claim 3.

6. The polyimide resin according to claim 5, wherein the side chain length of the polyimide resin is 0.8 to 1.5 times the long axis length of liquid crystal molecule and the length between side chains is 1.5 to 3.5 times the long axis length of the liquid crystal molecule.

7. A liquid crystal alignment film prepared by using the polyimide resin for vertical alignment material of liquid crystal display device as described in claim 5.

8. A liquid crystal display device comprising the liquid crystal alignment film as described in claim 7.

* * * * *